United States Patent [19]
Weadock

[11] Patent Number: 6,129,757
[45] Date of Patent: Oct. 10, 2000

[54] IMPLANTABLE MEMBERS FOR RECEIVING THERAPEUTICALLY USEFUL COMPOSITIONS

[75] Inventor: Kevin Weadock, Somerset, N.J.

[73] Assignee: Scimed Life Systems, Maple Grove, Minn.

[21] Appl. No.: 09/080,736

[22] Filed: May 18, 1998

[51] Int. Cl.⁷ .................................................. A61F 2/06
[52] U.S. Cl. ...................... 623/1.39; 623/1.42; 623/1.49; 623/901
[58] Field of Search .................................... 623/11, 12, 1, 623/16, 18, 901, 1.39, 1.42, 1.49

[56] References Cited

U.S. PATENT DOCUMENTS

| | | |
|---|---|---|
| 3,276,448 | 10/1966 | Kronentnal . |
| 3,400,719 | 9/1968 | Buddecke . |
| 3,483,016 | 12/1969 | McCool . |
| 3,953,566 | 4/1976 | Gore . |
| 3,962,153 | 6/1976 | Gore . |
| 4,233,360 | 11/1980 | Luck et al. . |
| 4,784,659 | 11/1988 | Fleckenstein et al. . |
| 4,822,361 | 4/1989 | Okita et al. . |
| 4,842,575 | 6/1989 | Hoffman, Jr. et al. . |
| 4,871,361 | 10/1989 | Kira . |
| 4,921,495 | 5/1990 | Kira . |
| 4,966,999 | 10/1990 | Coughli et al. ........................ 564/150 |
| 5,028,597 | 7/1991 | Kodama et al. . |
| 5,030,225 | 7/1991 | Aebischer et al. . |
| 5,034,265 | 7/1991 | Hoffman et al. . |
| 5,037,377 | 8/1991 | Alonso . |
| 5,131,907 | 7/1992 | Williams et al. . |
| 5,141,522 | 8/1992 | Landi . |
| 5,192,310 | 3/1993 | Herweck et al. . |
| 5,197,977 | 3/1993 | Hoffman, Jr. et al. . |
| 5,246,452 | 9/1993 | Sinnott . |
| 5,290,271 | 3/1994 | Jernberg . |
| 5,468,562 | 11/1995 | Fairvar et al. . |
| 5,474,797 | 12/1995 | Sioshansi et al. . |
| 5,492,763 | 2/1996 | Barry et al. . |
| 5,520,664 | 5/1996 | Bricault, Jr. et al. . |
| 5,536,656 | 7/1996 | Kemp et al. . |
| 5,624,704 | 4/1997 | Darouiche et al. ..................... 427/2.24 |
| 5,665,114 | 9/1997 | Weadock et al. . |
| 5,716,660 | 2/1998 | Weadock et al. . |

FOREIGN PATENT DOCUMENTS

| | | |
|---|---|---|
| 2169638 | 3/1995 | Canada . |
| 0 230 635 A3 | 5/1987 | European Pat. Off. . |
| 0 531 547 A1 | 3/1993 | European Pat. Off. . |
| 596615 | 5/1994 | European Pat. Off. . |
| 0 237 037 A2 | 8/1997 | European Pat. Off. . |
| 1 601 323 | 9/1970 | France . |
| 69 00 500 | 10/1970 | France . |
| 2 558 720 A1 | 2/1985 | France . |
| 1 491 218 | 4/1969 | Germany . |
| 1 494 939 | 6/1969 | Germany . |
| 153 685 | 8/1985 | United Kingdom . |
| WO 92/00110 | 1/1992 | WIPO . |
| WO 94/24298 | 10/1994 | WIPO . |
| WO 96/08149 | 3/1996 | WIPO . |

OTHER PUBLICATIONS

Billmeyer, Jr. F. "Pastics Technology", Textbook of Polymer Science, Third Edition, pp. 400–401, 457–469, 1984.

Kadletz, M., Moser, R., Preiss, P., Deutsch, M., Zilla, P. and Fasol, R., "In Vitro Lining of Fibronectin Coated PTFE Grafts With Cryopreserved Saphenous Vein Endothelial Cells." *Thorac. Cardiovasc; Suregon.* vol. 35, p. 143–147 (1987).

"Graft Complications in Relation to Prosthesis Healing", Lester R. Savage.

Product Specification sheet, Matrigel ® Basement Membrane Matrix, Becton Dickinson Labware.

"Graft Complications in Relation to Prosthesis Healing", Lester R. Savage.

Product Specification Sheet, MATRIGEL® Basement Membrane Matrix, Becton Dickinson Labware.

*Primary Examiner*—Mickey Yu
*Assistant Examiner*—Choon P. Koh
*Attorney, Agent, or Firm*—Hoffmann & Baron, LLP

[57] ABSTRACT

An implantable prosthesis includes a porous polymeric member having pores present in its wall structure wherein these pores contain a variety of therapeutically useful compositions including, collagen, genetically altered cells and piezoelectric materials. A process of preparing such a prosthesis is also disclosed.

12 Claims, No Drawings

IMPLANTABLE MEMBERS FOR RECEIVING THERAPEUTICALLY USEFUL COMPOSITIONS

FIELD OF THE INVENTION

The present invention relates to implantable members made from a porous polymeric material having a microstructure which can contain a variety of therapeutically useful materials and compositions. More specifically, the present invention relates to an implantable member, such as for example, a vascular graft having an ePTFE microstructure that is porous and which is able to accommodate a variety of materials including collagen, biological vectors, piezoelectric materials and the like.

BACKGROUND OF THE INVENTION

In the field of implantable prostheses, various porous polymeric extruded and textile materials have been used as substrates therefor. It is well known to coat the outer surfaces of such porous substrates with various compositions to enhance the biocompatibility of the prosthesis. For example, certain coatings can enhance the healing process by encouraging cellular ingrowth into the microporous structure and prevent bleeding from, e.g. suture holes made in the prosthesis, and/or deliver therapeutic agents to the site of implantation.

Examples of extruded tubular substrates which have been used as implantable prosthesis include, for example, polyurethane, polycarbonate and a fluorinated polymers such as polytetrafluoroethylene (PTFE). For example, expanded polytetrafluoroethylene (ePTFE) porous tubes are made by stretching and sintering and have been used as tubular prostheses for artificial blood vessels for a number of years. These polymeric tubes have certain advantages over conventional textile prostheses, but also have disadvantages of their own. An ePTFE tube has a microporous structure consisting of small nodes interconnected with many thin fibrils. The diameter of the fibrils, which depend on the processing conditions, can be controlled to a large degree, and the resulting flexible structure has greater versatility in many aspects than conventional textile grafts.

For example, ePTFE grafts can be used in both large diameter, i.e. 6 mm or greater artificial blood vessels, as well as in grafts having diameters of 5 mm or less. See, for example, co-owned U.S. Pat. No. 5,716,660 and U.S. Pat. No. 5,665,114 both of which are incorporated by reference herein.

One particular problem with ePTFE tubes, however, is their tendency to leak blood at suture holes and to propagate a tear line at the point of entry of the suture. As a result, numerous methods of orienting the node and fibril structure have been developed to prevent tear propagation. These processes are often complicated and require special machinery and/or materials to achieve this end.

Additionally, ePTFE arterial prostheses have been reported as suffering from poor cellular infiltration and collagen deposition of the microporous structure by surrounding tissue. Numerous attempts to achieve improved blood compatibility and tissue binding properties have thus far fallen short. For example, in a study reported by Guidoin, et al., cellular infiltration of the e-PTFE microporous structure was observed as being minimal. See "Histopathology of Expanded PTFE", Biomaterials 1993, Volume 14, No. 9.

In an attempt to produce viable endothelial cell monolayers on graft surfaces, cryopreserved cultivated human saphenous vein endothelial cells were cultivated on reinforced PTFE prostheses. Prior to seeding of the endothelial cells on the prostheses, the graft surface was precoated with human fibronectin. Such a process was reported to have discouraging results. See, Kadletz, et al. in "In vitro lining of Fibronectin Coated PTFE Grafts With Cryopreserved Saphenous Vein Endothelial Cells", Thorac. Cardiovasc. Surgeon 35 (1987) 143–147.

Grafts having a monolayer of cells disposed on an outer surface thereof, however, are ineffective because the cells are easily sloughed off the graft. In particular, seeding the surface of a graft with cells results in poorly formed basement membrane which results in the loss of a significant number of cells from the surface of the graft.

More recently a study using laminin, collagen type I/III, as well as fibronectin as a precoating material prior to seeding of endothelial cells on ePTFE grafts was performed by Kaehler et al. This study reported that cell adherence and cell spreading were distinctly superior on the surfaces which were precoated with fibronectin/type I/III collagen. See "Precoating Substrate and Surface Configuration Determine Adherence and Spreading of Seeded Endothelial Cells on Polytetrafluoroethylene Grafts", Journal of Vascular Surgery, Volume 9, No. 4 April (1989).

In addition to coating implantable prostheses with, for example, extracellular matrix proteins, such as collagen, attempts have been made to implant polymeric piezoelectric materials within the body to stimulate the healing process. In particular, when a piezoelectric material is subjected to a mechanical stress, it produces an electrical field. Such electrical fields are known to stimulate cell growth. For example, piezoelectric films and membranes have been developed for ossification enhancement and regenerating severed nerves. See, U.S. Pat. Nos. 5,298,602 and 5,030,225 respectively. Such films and membranes, however, are often difficult to manufacture and are limited in their application to the body.

Accordingly, there is a need for a porous implantable device which is capable of acting as a support for a variety of therapeutically useful substrates. In particular, it would be desirable to have a porous implantable material that can contain or be substantially filled with a fluid which solidifies and is cross-linkable to form an insoluble, biocompatible, biodegradable material, such as collagen. There is also a need for an implantable device made from a porous polymeric material which is able to accommodate a fluid which contains one or more populations of cells that can produce and secrete therapeutically useful agents into the local environment. Still further, there is a need for an implantable device made from a porous polymeric material which can accommodate a piezoelectric composition which has the ability to stimulate cell ingrowth via the generation of electrical fields in response to mechanical stress. The present invention is directed to meeting these and other needs.

SUMMARY OF THE INVENTION

The present invention relates to an implantable member that includes a porous polymeric substrate that has a wall structure. The wall structure has pores filled with a fluid which solidifies and is cross-linkable to form an insoluble, biocompatible, biodegradable material that is insoluble at a pH of about 7.4.

Another embodiment of the present invention includes a porous polymeric substrate which has a wall structure that includes pores filled with a fluid containing one or more populations of cells.

A further embodiment of the present invention includes a porous polymeric substrate that has a wall structure which includes pores that are filled with a piezoelectric composition.

DETAILED DESCRIPTION OF THE PREFERRED EMBODIMENT

The present invention is an implantable member that has a porous polymeric substrate that includes a wall structure. The wall structure has pores which are filled with various therapeutically useful materials, such as for example, insoluble, biodegradable, biocompatible materials, biologically active vectors, cells and piezoelectric compositions.

The porous polymeric substrates of the present invention include various biocompatible polymers which are or can be rendered porous. These porous polymeric substrates include, for example, polyurethane, fluorinated hydrocarbons, polycarbonates, polyethylenes, polypropylenes, polyvinyl chlorides, polyvinyl acetates, polystyrenes, polyureas, silicone rubbers, polyamides, polyaldehydes natural rubbers, poly-ester copolymers, styrene-butadiene copolymers and combinations thereof. Thus, specific examples of porous polymeric substrates suitable for use in the present invention include, polytetrafluoroethylene, poly(ethylene terephthalate) and copolymers thereof.

Fluorinated hydrocarbons include, for example, fluorinated ethylene propylene polymers, perfluoroalkoxytetrafluoroethylene, as well as polytetrafluoroethylene, all of which are capable of being extruded, stretched and sintered to form porous walled tubular structures, such as for example, expanded polytetrafluoroethylene (ePTFE). For purposes of the present invention, the term implantable member includes tubular prostheses, such as for example, vascular prostheses including grafts, composite graft-stent devices, endovascular prostheses and other tubular prostheses useful as implantable devices for the repair, maintenance or replacement of conduit vessels in the body. Such implantable members also function as support structures for delivering therapeutically useful substrates to targeted areas. These therapeutically useful substrates include, for example, collagen, certain cells and piezoelectric compositions. The preferred implantable members of the present invention are those used in the vascular system. While tubes for vascular use are a preferred embodiment of the present invention, sheets and other structures are also within the scope of the present invention and can be used during, for example, hernia repair or repair of the myocardium.

The insoluble, biocompatible, biodegradable materials of the present invention are generally extracellular matrix proteins which are known to be involved in cell-to-cell and cell-to-matrix interactions including cell-cell and cell-matrix adhesion. These materials include for example, collagen, gelatin, vitronectin, fibronectin, laminin, reconstituted basement membrane matrices such as those marketed under the trademark MATRIGEL® by Collaborative Biomedical Products, Inc. of Bedford, Mass. and derivatives and mixtures thereof. All of these extracellular matrix proteins are capable of being introduced into the pores or voids of the porous polymeric substrates of the present invention, preferably as a liquid, and precipitated out to form a solid. These biocompatible, biodegradable materials may then be cross-linked to form body fluid insoluble materials. Alternately, these biocompatible, biodegradable materials may be introduced into the pores/voids of the polymeric substrates in solid form using fluid-pressure or other techniques such as precrosslinking. As used herein the term "biodegradable" means it will break down and/or be absorbed in the body. These biocompatible, biodegradable materials preferably substantially fill the voids of for example, an ePTFE wall of an implantable member of the present invention and provide a binding substrate of natural origin on which surrounding tissue can easily attach. Rather than merely coat a surface of the polymeric substrate surface, these materials are intended to serve as fillers for the pores/voids.

One of the advantages to using ePTFE as the material from which implantable members of the present invention are made is ePTFE's natural antithrombogenic properties. While the inherent surface chemistry of ePTFE promotes antithrombogenicity, permanent attachment of the neotima of cells is generally compromised. For example, an outer capsule of perigraft material forms easily around the outer surface of ePTFE implantable members but may be easily stripped away. Typically, only a very thin inner capsule is formed on the intraluminal surface of a ePTFE graft as compared with a conventional textile graft. When this happens, embolization may occur if some or all of the neotima detaches and becomes trapped in small blood vessels. Additionally, suture holes in the walls of a ePTFE prosthesis generally require compression or topical pressure to accomplish hemostasis.

It is apparent, therefore, that the implantable members of the present invention must reach a balance between the natural antithrombogenic properties of, for example, ePTFE and the properties of, for example, collagen which may tend to contribute somewhat to thrombosis formation, while providing a better blood-tight binding surface for tissue ingrowth.

In preparing the implantable members of the present invention, a fluid or solution of a biocompatible, biodegradable material is formed. The extracellular matrix proteins which are used in the fluid/solution may be soluble. Some of these materials, however, may be difficult to dissolve in water. Collagen, for example, is considered insoluble in water, as is gelatin at ambient temperature. To overcome such difficulties, collagen or gelatin may be preferably formed at an acidic pH, i.e. at a pH less than 7 and preferably at a pH of about 2 to about 4. The temperature range at which such fluids/solutions are formed is between about 4° C. to about 40° C., and preferably about 30° C.–35° C.

Type I collagen is the preferred collagen used in the present invention, although other types are contemplated. An important property of collagen is that it initiates the clotting response when exposed to whole blood. Thus, collagen present in the pores/voids of an implantable member of the present invention contributes to inhibition of e.g., prosthesis leakage, as well as to healing of the area surrounding the implant during and immediately after implantation.

Once the biocompatible, biodegradable material is introduced into the pores of a porous polymeric substrate it solidifies therein. As used herein, the term "solidifies" means that the biodegradable material is precipitated out into solid form, the biodegradable material is optionally cross-linked. Alternatively, the solidifications can be accomplished by other standard chemical reactions that are compatible with the present invention. Cross-linking of the material can be accomplished by any conventional method so long as it is not disruptive of or have a negative effect on the porous polymeric substrate. In the case of collagen, for example, cross-linking can be accomplished by exposure to aldehyde vapor followed by drying to remove excess moisture and aldehyde. Alternatively, the collagen may be pre-crosslinked prior to introduction into the pores/voids via a dispersion. In the case of gelatin, cross-linking is effectuated by similar methods.

The biocompatible, biodegradable material can be introduced into the pores of such a porous polymeric substrate by any conventional method. For example, a force can be used to cause the solution of the biocompatible material to penetrate into the walls of the implantable member, thereby contacting the internodal voids. This can be accomplished in a number of ways, such as by clamping one end of a tubular prosthesis, filling the inner lumen with a dispersion of the biocompatible, biodegradable material and using pressure to cause migration of the dispersion into the interstices of the walls of the porous polymeric substrate. The transluminal flow of the dispersion is believed to permit sufficient contact between the biocompatible, biodegradable materials and the voids of the porous polymeric substrate.

While the time for impregnation depends on the nature of the porous polymeric substrate used, its pore size, graft length, impregnation pressure, concentration of the material and other factors, generally it can be accomplished in a short period of time, for example, from less than 1 minute to 10 minutes at a preferred temperature range of about 30° C. to about 35° C. These parameters are not critical, however, provided the pores/voids are substantially filled with e.g., the biocompatible, biodegradable material. As set forth previously, the soluble biocompatible, biodegradable material may be optionally subjected to cross-linking treatment such that it is solidified in place. For example, cross-linking by exposure to various cross-linking agents and methods such as formaldehyde vapor is then preferably carried out. Subsequent to formation of the cross-linked material, the implantable member can then be rinsed and prepared for sterilization by known methods. Vacuum drying or heat treatment to remove excess moisture and/or cross-linking agents can then be used. The entire process of contacting the porous polymeric substrate/solution can be repeated several times, if necessary, to achieve the desired impregnation.

In a preferred embodiment, the surface of the porous implantable substrate can be chemically modified to impart greater hydrophilicity thereto. For example, this can be accomplished by glow discharge plasma treatment or other means whereby hydrophilic moieties are attached to or otherwise associated with the porous polymeric substrate surface. Such treatment enhances the ability of the porous polymeric substrate to imbibe the biocompatible dispersion/solution.

In a similar fashion, the surface of the porous polymeric substrate can be modified using, for example, conventional silver ion assisted beam deposition processes to render the surface of the porous polymeric material more antimicrobial. In such a process, silver is deposited onto the surface of the porous polymeric material via silver ion assisted beam deposition prior to filling the pores of the porous polymeric material with a insoluble, biocompatible, biodegradable material. Such an ion assisted beam deposition process is set forth in U.S. Pat. Nos. 5,468,562, 5,474,797, 5,492,763 and 5,520,664 to Spire Corporation all of which are incorporated by reference herein.

In addition to the insoluble, biocompatible, biodegradable material set forth previously, other materials can be integrated into the pores of polymeric substrate. For example, various pharmacological actives such as antimicrobials, antivirals, antibiotics, growth factors, blood clotting modulators such as heparin and the like, as well as mixtures and composite layers thereof can be applied in liquid/fluid form into the pores of the polymeric substrate.

Alternatively, the fluid which fills the pores of the polymeric substrate can include thrombo-resistant agents, antibiotic agents, antitumor agents, growth hormones, antiviral agents, anti-angiogenic agents, angiogenic agents, anti-amitotic agents, anti-inflammatory agents, cell cycle regulating agents, hormones, their homologs, derivatives, fragments, pharmaceutical salts and combination thereof.

The thrombo-resistant agents of the present invention can include, for example, heparin, heparin sulfate, hirudin, hyaluronic acid, chondroitin sulfate, dermatan sulfate, keratan sulfate, lytic agents, including urokinase and streptokinase their homologs, analogs, fragments, derivatives and pharmaceutical salts thereof.

The antibiotic agents of the present invention include, for example, penicillins, cephalosporins, vancomycins, aminoglycosides, quinolones, polymyxins, erythromycins, tetracyclines, chloramphenicols, clindamycins, lincomycins, sulfonamides their homologs, analogs, derivatives, pharmaceutical salts and mixtures thereof.

The anti-tumor agents of the present invention include, for example, paclitaxel, docetaxel, alkylating agents including mechlorethamine, chlorambucil, cyclophosphamide, melphalan and ifosfamide; antimetabolites including methotrexate, 6-mercaptopurine, 5-fluorouracil and cytarabine; plant alkaloids including vinblastine, vincristine and etoposide; antibiotics including doxorubicin, daunomycin, bleomycin, and mitomycin; nitrosureas including carmustine and lomustine; inorganic ions including cisplatin; biological response modifiers including interferon; angiostatin agents and endostatin agents; enzymes including asparaginase; and hormones including tamoxifen and flutamide their homologs, analogs, fragments, derivatives, pharmaceutical salts and mixtures thereof.

The anti-viral agents of the present invention include, for example, amantadines, rimantadines, ribavirins, idoxuridines, vidarabines, trifluridines, acyclovirs, ganciclovirs, zidovudines, foscarnets, interferons their homologs, analogs, fragments, derivatives, pharmaceutical salts and mixtures thereof.

The anti-mitotic agent of the present invention can include, for example, a radioactive material which may be coupled to a biologically compatible carrier, such as for example, albumin.

Both α- and β-emitting isotopes are examples of radioactive materials that can be used in conjunction with the present invention. Such β-emitting isotopes include, for example, $^{32}P$, $^{131}I$, $^{90}Y$ and mixtures thereof. Any conventionally known isotope, however, which has therapeutic value can be used in connection with the present invention.

A preferred method of preparing the implantable members of the present invention includes preparing a mixture, i.e. a solution or dispersion of a known concentration of a biocompatible, biodegradable material which includes, for example, collagen, gelatin, derivatives of collagen, derivatives of gelatin and mixtures thereof, having a pH within a range of from about 2 to about 4 and preferably a pH of about 3.5–3.9. Such a composition should have a low ionic strength, and be prepared at temperatures of about 4° C. to about 40° C., and preferably about 30° C. to about 35° C.

The surface of the implantable member is preferably modified by enhancing the hydrophilicity thereof with glow discharge plasma deposition prior to contacting the implantable members with the biocompatible, biodegradable material. The implantable member, such as for example a vascular or endovascular prosthesis is then contacted under force with the biocompatible, biodegradable material to allow for impregnation and transluminary flow thereof through the walls of the prosthesis, thereby substantially filling the interstitial voids. The prosthesis is then treated with a chemical solution, such as buffered phosphate at a pH of about 7.4, to insolubilize the biocompatible material in place. Optionally, subsequent formaldehyde vapor exposure can be used to cross-link the material once it is deposited in the voids.

In another embodiment of the present invention, an implantable member is provided which includes a porous polymeric substrate that has a wall structure that can be filled with a fluid containing one or more populations of cells. The porous polymeric substrate of the implantable member has been described previously. In this embodiment, however, biologically active vectors, such as cells, which are able to survive within the body are dispersed within the pores of the walls of the porous polymeric substrate. These cells themselves may be therapeutically useful or they may be selected or engineered to produce and release therapeutically useful compositions.

For purposes of the present invention, "biologically active vector" means any biologically compatible vehicle which can be introduced within a mammalian body and which is able to produce and release one or more therapeutically useful compositions. The production and/or release of such therapeutically useful compositions can be passive, i.e., continuously produced and/or released; or active, i.e., release and/or production is controlled by, e.g., secondary agents introduced into the system which serve to turn "on" and "off" the production and/or release of the therapeutic is compositions.

As set forth above, the biological vectors of the present invention can include cells, such as for example, cells derived from a mammal. Such cells may be autologously or non-autologously derived. In a preferred embodiment, the cells are endothelial cells, such as for example, vascular smooth muscle cells.

Such cells may be therapeutically beneficial alone or they can be genetically altered by introducing an exogenous genetic construct into the cell through, conventional techniques, such as for example, transfection. Such genetic constructs may take any conventional form, such as for example, single or double stranded DNA or RNA. These genetic constructs can be from, for example, genomic, plasmid or of any other origin. In a preferred embodiment, the biological vector of the present invention is transfected with a genetic construct which codes for a secreted form of tissue plasminogen activator.

Thus, implantable members which have transfected cells dispersed within the pores of their walls are able to release therapeutically useful compositions directly at the site of implantation, to for example, decrease the likelihood of clot formation or to decrease the size of a clot that might form thereat.

In another embodiment of the present invention, a porous polymeric substrate, as previously described, has a wall structure that includes pores which are filled with a piezoelectric composition. For purposes of the present invention, the term "piezoelectric composition" as used herein, is intended to encompass natural and synthetic materials which are capable of generating electrical charges on their surface when subjected to mechanical strain. Thus, for purposes of the present invention, any material which generates an electrical charge in response to a mechanical strain is to be considered a piezoelectric composition. When used in conjunction with the present invention, such piezoelectric compositions must be biodegradable. Furthermore, such compositions must be capable of being dispersed within the pores of the porous polymeric substrates of the present invention.

Suitable piezoelectric compositions include, for example, polypeptide polymers, electret polymers and ferroelectric polymers. Other suitable piezoelectric compositions for use with the implantable members of the present invention include, for example biodegradable polyepsilon amino caprolactone, polyhydroxybutyrate, polyvinylidene fluoride, polyvinyl fluoride, vinylidene fluoridetrifluoroethylene copolymer, vinylidene cyanide-vinyl acetate copolymer, polyvinyl chloride, polylactic acid, collagen, nylon 11, polygamma benzylglutamate, polygamma methylglutamate, copolymers of trifluoroethylene, copolymers and derivatives thereof.

Where such piezoelectric materials are dispersed within the pores of a porous polymeric substrate according to the present invention, they are able to regulate cell growth. In particular, when an implantable member of the present invention, such as for example, a vascular or endovascular prosthesis, is treated with a piezoelectric material, and then implanted in, e.g. a mammal, an electric field will be generated as the blood pressure of the patient exerts a stress on the walls of the prosthesis. This electric field, in turn, stimulates the growth of for example, endothelial cells and fibroblasts, throughout the wall structure of the porous vascular graft which, in turn enhances the healing process thereof.

Although illustrative embodiments of the present invention have been described herein, it should be understood that the invention is not limited to those described, and that various other changes or modifications may be made by one skilled in the art without departing from the scope or spirit of the invention.

What is claimed is:

1. An implantable member comprising a porous polymeric substrate having a wall structure substantially free of ePTFE nodes and fibrils structure, said wall structure having pores filled with a fluid composition that contains one or more substances which are precipitated out in situ to form an insoluble, biocompatible, biodegradable material therein.

2. The implantable member of claim 1, wherein said substances are selected from the group consisting of thrombo-resistant agents, antibiotic agents, anti-tumor agents, growth hormones, antiviral agents, anti-angiogenic agents, angiogenic agents, anti-mitotic agents, anti-inflammatory agents, cell cycle regulating agents, genetic agents, hormones, their homologs, derivatives, fragments, pharmaceutical salts, and combinations thereof.

3. The implantable member of claim 2, wherein said thrombo-resistant agents are selected from the group consisting of heparin, heparin sulfate, hirudin, hyaluronic acid, chondroitin sulfate, dermatan sulfate, keratan sulfate, lytic agents, including urokinase and streptokinase their homologs, analogs, fragments, derivatives and pharmaceutical salts thereof.

4. The implantable member of claim 2, wherein said antibiotic agents are selected from the group consisting of penicillins, cephalosporins, vancomycins, aminoglycosides, quinolones, polymyxins, erythromycins, tetracyclines, chloramphenicols, clindamycins, lincomycins, sulfonamides their homologs, analogs, derivatives, pharmaceutical salts and mixtures thereof.

5. The implantable member of claim 2, wherein said anti-tumor agents are selected from the group consisting of paclitaxel, docetaxel, alkylating agents including mechlorethamine, chlorambucil, cyclophosphamide, melphalan and ifosfamide; antimetabolites including methotrexate, 6-mercaptopurine, 5-fluorouracil and cytarabine; plant alkaloids including vinblastine, vincristine and etoposide; antibiotics including doxorubicin, daunomycin, bleomycin, and mitomycin; nitrosureas including carmustine and lomustine; inorganic ions including cisplatin; biological response modifiers including interferon; angiostatin agents and endostatin agents; enzymes including asparaginase; and hormones including tamoxifen and flutamide their homologs, analogs, fragments, derivatives, pharmaceutical salts and mixtures thereof.

6. The implantable member of claim 2, wherein said anti-viral agents are selected from the group consisting of amantadines, rimantadines, ribavirins, idoxuridines, vidarabines, trifluridines, acyclovirs, ganciclovirs, zidovudines, foscarnets, interferons their homologs, analogs, fragments, derivatives, pharmaceutical salts and mixtures thereof.

7. The implantable member of claim 1, wherein said polymeric substrate is selected from the group consisting of polyurethanes, polycarbonates, polyethylenes, polypropylenes, polyvinyl chlorides, polyvinyl acetates, polystyrenes, polyureas, silicone rubbers, polyamides, polyaldehydes, natural rubbers, polyether-ester copolymers, styrene-butadiene copolymers, and combinations thereof.

8. The implantable member of claim 1, wherein said insoluble, biocompatible, biodegradable material includes gelatin.

9. The implantable member of claim 1, wherein said insoluble, biocompatible, biodegradable material includes extracellular matrix proteins.

10. The implantable member of claim 9, wherein said extracellular matrix proteins are selected from the group consisting of collagen, including collagen Type I, collagen Type II, collagen Type III, collagen Type IV, and collagen Type V, vitronectin, fibronectin, laminin, reconstituted basement membrane matrices, and derivatives and mixtures thereof.

11. The implantable member of claim 1, wherein a surface of said polymeric substrate is subjected to a silver ion-beam-assisted deposition process to render said substrate more antimicrobial.

12. The implantable member of claim 11, wherein silver is deposited onto said substrate via said ion-beam-assisted deposition process prior to filling said pores with said insoluble, biocompatible, biodegradable material.

* * * * *

UNITED STATES PATENT AND TRADEMARK OFFICE
CERTIFICATE OF CORRECTION

PATENT NO. : 6,129,757
DATED : October 10, 2000
INVENTOR(S) : Weadock, Kevin

It is certified that error appears in the above-identified patent and that said Letters Patent are hereby corrected as shown below:

At column 7, line 31, the printed patent incorrectly reads "therapeutic is compositions.". The patent should read --therapeutic compositions.--.

Signed and Sealed this

Fifteenth Day of May, 2001

*Attest:*

NICHOLAS P. GODICI

*Attesting Officer*    *Acting Director of the United States Patent and Trademark Office*